United States Patent [19]

Caprio, Jr. et al.

[11] Patent Number: 5,656,023
[45] Date of Patent: Aug. 12, 1997

[54] ADJUSTABLE KNEE SUPPORT

[75] Inventors: Louis Caprio, Jr., Revere; Stephen Madow, Swampscott, both of Mass.

[73] Assignee: Tru-Fit Marketing Corporation, Lynn, Mass.

[21] Appl. No.: 407,168

[22] Filed: Mar. 21, 1995

Related U.S. Application Data

[63] Continuation of Ser. No. 28,968, Mar. 10, 1993, Pat. No. 5,399,153, which is a continuation-in-part of Ser. No. 776,193, Oct. 15, 1991, Pat. No. 5,221,252.

[51] Int. Cl.$^6$ ........................................................ A61F 5/00
[52] U.S. Cl. ................................. 602/63; 602/26; 602/62
[58] Field of Search ............................... 602/5, 26, 60–63

[56] References Cited

U.S. PATENT DOCUMENTS

| | | |
|---|---|---|
| 2,858,540 | 5/1958 | Morrison . |
| 3,046,981 | 4/1962 | Biggs, Jr. et al. . |
| 3,092,110 | 6/1963 | Duensing . |
| 3,189,919 | 6/1965 | Chase . |
| 3,406,406 | 10/1968 | Lutz . |
| 3,613,681 | 10/1971 | Adams . |
| 3,677,265 | 7/1972 | Brabazon . |
| 3,804,084 | 4/1974 | Lehman . |
| 3,934,583 | 1/1976 | Hollingshead et al. . |
| 3,945,046 | 3/1976 | Stromgren . |
| 3,945,047 | 3/1976 | Jarrell, Jr. . |
| 4,013,070 | 3/1977 | Harroff . |
| 4,084,584 | 4/1978 | Detty . |
| 4,296,744 | 10/1981 | Palumbo . |
| 4,353,362 | 10/1982 | DeMarco . |
| 4,378,009 | 3/1983 | Rowley et al. . |
| 4,407,276 | 10/1983 | Bledsoe . |
| 4,423,720 | 1/1984 | Meier et al. . |
| 4,651,722 | 3/1987 | Karczewski . |
| 4,724,831 | 2/1988 | Huntjens . |
| 4,765,318 | 8/1988 | Tranberg et al. . |
| 5,024,216 | 6/1991 | Shiono . |
| 5,086,761 | 2/1992 | Ingram . |
| 5,139,476 | 8/1992 | Peters . |
| 5,139,477 | 8/1992 | Peters . |

FOREIGN PATENT DOCUMENTS

| | | |
|---|---|---|
| 101132 | 3/1965 | Denmark . |
| 2 622 437 | 2/1987 | France . |
| 3511250A1 | 7/1985 | Germany . |

OTHER PUBLICATIONS

Carole Wright Gifts, 1991, Advertisement "Therapeutic Knee Brace".

*Primary Examiner*—Linda C. Dvorak

[57] ABSTRACT

An adjustable knee support is formed from a single piece of a resilient, flexible laminate, preferably a layer of neoprene bonded to a nylon outer casing and a nylon inner lining. A central portion of the support overlies the patella. Upper and lower fasteners are integral with the central portion above and below the knee. Each fastener includes at least one strap that extends laterally and a strap extension that wraps around the leg. The upper and lower fasteners extend in opposite directions. The central portion has a separate pair of fastening straps which extend transversely from both sides and meet behind the knee cap. Tabs carrying an array of hook-type fastenings are secured to the free end of each strap and strap extension. The upper and lower straps and their extensions are separated from the central fastener by a cutout portion of sufficient vertical height to allow the support to flex without the buckling or rubbing the back of the leg. By pulling each of the straps separately and then securing the tab on the outer casing it is possible to adjust the degree of compression at each of the three vertical locations independently. The strap extensions have highly elastic portions to accommodate normal expansions and contractions of the leg. The central portion includes pockets with flexible metallic stays located in opposite sides of the patella to provide enhanced mechanical support.

11 Claims, 3 Drawing Sheets

ADJUSTABLE KNEE SUPPORT

REFERENCE TO RELATED APPLICATIONS

This is a continuation of application Ser. No. 08/028,968 filed on Mar. 10, 1993, now U.S. Pat. No. 5,399,153, which is a continuation-in-part of U.S. Ser. No. 07/776,193, filed Oct. 15, 1991, now U.S. Pat. No. 5,221,252.

BACKGROUND OF THE INVENTION

This invention relates in general to an elastic supports. More specifically, it relates to an elastic knee support that provides a direct and independently adjustable compressive force on the knee cap while accommodating changes in the circumference of the calf and thigh and providing enhanced support.

A wide variety of orthopedic appliances and elastic braces are known. They are used to support an injured knee. They also can be used on healthy knees to support and thereby reduce the likelihood of injury to the knee and surrounding tissue, particularly when the user is engaged in a sports or occupational activity that subjects the knee to unusual stretching or load bearing. However, orthopedic appliances and orthopedic braces are generally not used by the general public for minor sprains or to protect a healthy knee during strenuous activities.

Taping of a knee, whether to promote healing or to protect a knee prophlylactically, is known, but correct taping requires skill and is time consuming. Moreover, it often interferes with normal movement of the knee, chafes, and is painful to remove. Orthopedic appliances, on the other hand, are typically cumbersome devices having articulated metal supports. These devices are heavy, expensive and uncomfortable to wear. They also typically attach to the leg over a substantial portion of the thigh and calf, typically at least twelve inches at both locations. U.S. Pat. No. 4,407,276 to Bledsoe is exemplary of these appliances.

A wide variety of orthopedic brace designs using resilient materials and no articulated metal members have also been proposed. Some are used commercially. One approach has been to use a sleeve or patch formed totally or in part of an elastic material reinforced by, or supporting rigid or somewhat flexible members or cushioning pockets. U.S. Pat. Nos. 3,189,919; 3,677,265; 3,934,583; 3,945,047 and 4,765,318 describe braces of this general type. Another style is to use multiple elastic wrappings and/or long straps wrapped in criss-cross fashion in an attempt to fix the brace reliably on the leg and to develop some compressive force while a greater freedom of movement than with other appliances or braces. U.S. Pat. Nos. 3,046,989 and 3,945,046 are braces of this general type. U.S. Pat. No. 4,378,009 discloses a brace formed as an elongated plastic tube which can be wrapped around a body part. The tube can be solid or inflatable. In one form it is formed in a sheet of vinyl having Velcro mounting tabs to hold the assembly in place when it is wrapped around a leg. One frequent disadvantage of braces formed of multiple components is that the edges or seams can pinch the skin or rub it as the knee is flexed. Another disadvantage is that known braces do not provide a direct compressive force on the patella that is adjustable and is independent of the arrangement that secures the brace in a desired position or the leg.

U.S. Pat. No. 4,353,362 to DeMarco discloses an "unfolding type", wrap-on brace with oppositely directed tapes and Velcro-type fasteners above and below the kneecap. The brace has inbuilt, K-shaped stays on opposite sides of the kneecap to increase the rigidity of the support. The tapes are wrapped multiple times around the thigh and calf and then secured using the fasteners. While DeMarco avoids some of the problems of prior art braces, it does not provide an adjustable compressive force that is applied directly to the kneecap (patella) or a compressive force that is independent of securing of the support on the leg or knee.

Perhaps the most common form of orthopedic knee support (not brace) sold commercially is simply a tubular sleeve of an elastic material that pulls over and grips the knee and adjoining regions. While this device is simple, it must be manufactured in a variety of sizes in order to fit the normal range of adult leg sizes properly. Moreover, even if properly sized these supports can slide up or down the leg during use. They also buckle and chafe the skin during flexure of the knee. U.S. Pat. No. 4,084,584 to Detty discloses a type of elastic sleeve support with a padded opening around the patella and a two piece construction secured by a pair of vertical seams. This support can buckle and chafe. Also, it does not provide an independently adjustable compressive force directly on the patella.

It is also known to manufacture a simple tubular support where one portion of the support, below the knee, is a tube of an elastic material and a portion above the knee is wrapped around the leg and is secured by a Velcro tab. While the upper wrap introduces some adjustability, this support nevertheless must be sold in a variety of sizes. Also, it provides no direct compressive support for the patella, let alone an adjustable compressive support.

It is therefore a principal object of this invention to provide a lightweight, flexible knee support that provides a direct and adjustable compressive force on the patella and/or immediately surrounding tissue.

A further principal object is to provide a support with the foregoing advantages that is made in a single size, yet fits all wearers within a broad grouping with a tailored fit that is comfortable and reliably locates the support on the leg.

Another object of the invention is to provide a support with all of the foregoing advantages which does not irritate the user with seam bite, buckling or rubbing at the back of the knee, even through repeated flexures of the knee through a full range of motion.

A further object is to provide a support with the foregoing advantages which accommodates expansions and contractions of the thigh and calf during use.

A further object is to provide all of the foregoing advantages while at the same time providing enhanced mechanical support for an injured knee as compared to conventional tubular sleeve supports formed exclusively of a resilient woven and/or elastic materials.

A still further object is to provide all of the foregoing advantages at a competitive cost of manufacture using known materials and fabrication techniques.

SUMMARY OF THE INVENTION

A one-piece, one-size-fits-all elastic knee support is formed from a sheet of an elastic material, preferably neoprene and preferably with a nylon outer casing and an inner nylon lining. A central portion of the support bears directly on the patella and/or its surrounding tissue. The sides of this central portion terminate in integral fastening straps that wrap around the knee. A tab of "hook" type fastener material is preferably sewn onto the end of one of these central straps to secure it reliably to the end of the opposite central strap. The degree of overlap of the central straps when secured determines the size and level of compressive force exerted directly by the central portion on the patella.

Upper and lower fasteners preferably formed integrally with the central portion secure the support to the leg immediately above and below the knee. Each fastener has a face portion that lies on the front of the leg and a strap that extends perpendicular to the leg. A tab of hook-type fastener material sewn onto the free end of each strap releasably grips a strap extension that wraps around a calf or thigh. The strap includes a section of a highly resilient material and an end portion that carries another tab of hook-type fastener material. The end portion releasably secures to the nylon outer casing of the face portion of the fastener. The location of the tab on the face portion, in combination with the elastic force of the material forming the fastener, develops sufficient compressive force to secure the support in a preselected position on the leg reliably. The flexibility and elasticity of the upper, lower and central fasteners allow them to mold themselves to the contours of the users leg while developing any of a range of preselected compressive forces encircling the leg. The resilient portion of the strap extensions allows the calf and thigh to expand, e.g. to accommodate the expansion of during an athletic activity, or the swelling of injured tissue through stretching of the resilient portion. This resilient expansion avoids readjusting the support or a constriction of the limbs that can interfere with blood circulation if there is no enlargement of the support. After use, e.g. where the user sits or reclines, contraction of the thigh and calf are automatically accommodated by the contraction of the resilient portion. The contraction maintains the compressive force that holds the support in a preselected location on the leg.

A cut-out or generally V-shaped gap separates each upper and lower strap from the adjacent central straps, which also extend generally perpendicular to the leg. The cut-outs are open at the lateral edges of the support when it is flat. The strap extensions are sufficiently narrow that they do not cover or otherwise interfere with the action of these cutouts.

The central support portion can be closed covering the patella, or open, with a hole formed at the patella, preferably with an encircling pad at the edge to locate the opening on the patella and distribute the compressive force of the stretched neoprene in the central portion and central straps to the region immediately surrounding the patella. The central portion preferably includes two pairs of pockets that lie on opposite sides of the patella and each hold flexible, flat metallic stays. The stays allow the full flexure of the support, but provide an enhanced degree of support for an injured knee.

The upper and lower straps preferably extend in opposite directions to stabilize the position of the fastened support on the leg. The upper and lower straps extend vertically about four inches above and below the knee. The central straps have a minimum height of about two inches where they overlap behind the knee. The cut-outs each leave a gap of about one inch directly behind the knee. The strap extensions preferably extend at least eighteen inches from the associated tab and include a resilient stretch section of about three inches length. They have a width of approximately two inches.

These and other features of the invention will be more fully understood from the following detailed description which should be read in light of the accompanying drawings.

DETAILED DESCRIPTION OF THE PREFERRED EMBODIMENTS

Figure 1:
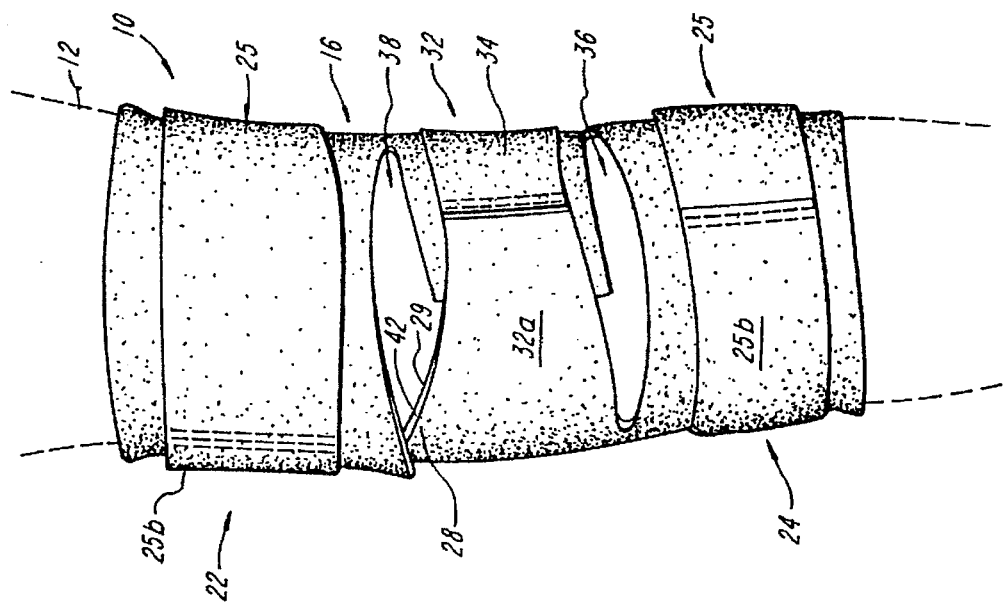
FIG. 1 is a view in perspective of the front and one side of a knee support according to the present invention secured on a leg to support the knee.
Figure 2:
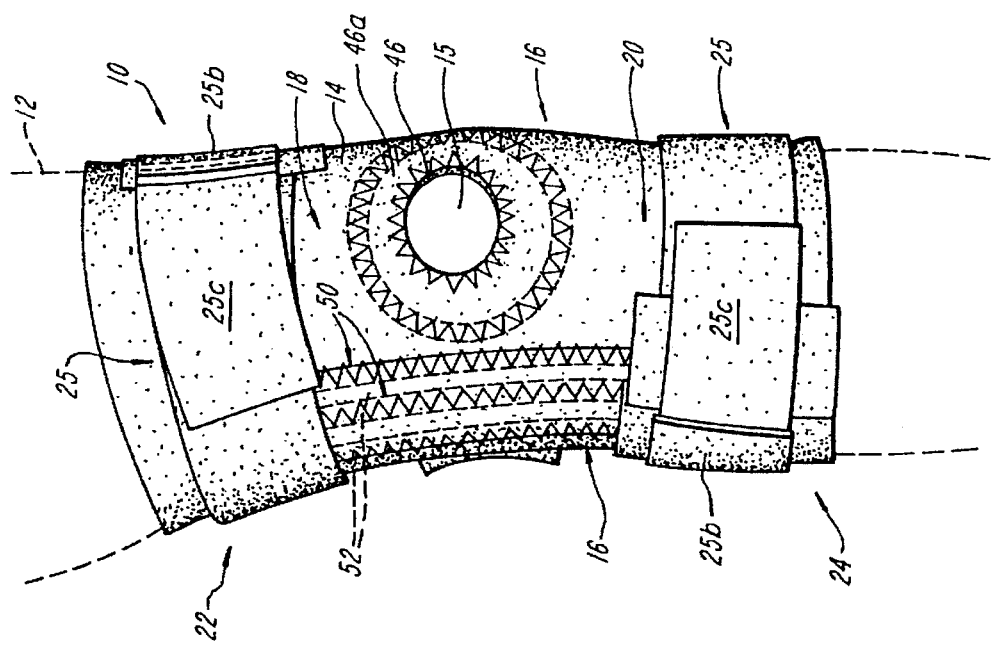
FIG. 2 is a view in perspective of the rear of the support shown in FIG. 1.

FIGS. 1 and 2 show a knee support 10 according to the present invention secured on a leg 12. A central portion 14 of the support is positioned over a knee cap or patella 15, and the tissue surrounding the patella. The central portion has sides 16,16, an upper edge 18 and a lower edge 20. An upper fastener 22 includes a front portion 22a and a strap portion 22b. A lower fastener 24 includes a front portion 24a and a strap portion 24b. These fasteners, in part, secure the support to the leg at the lower thigh and upper calf, respectively. Each strap has a free end 22c or 24c. A generally circular opening 46 that encircles the patella. This "open" support preferably includes a circular cushion sewn 46a into the edge of the opening to support the patella laterally or to support the tissue surrounding the patella more directly.

Figure 3:
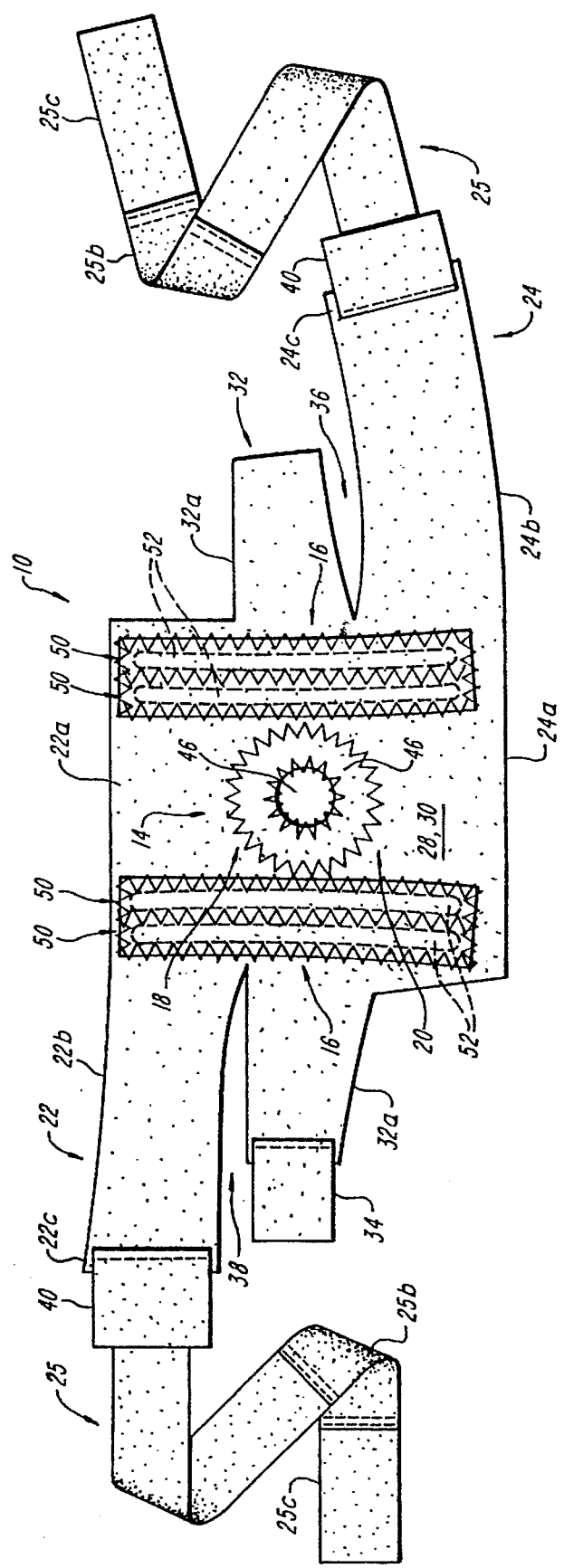
FIG. 3 is a plan view of outside of the knee support of FIGS. 1 and 2 when it is unfastened and laid flat.
Figure 4:
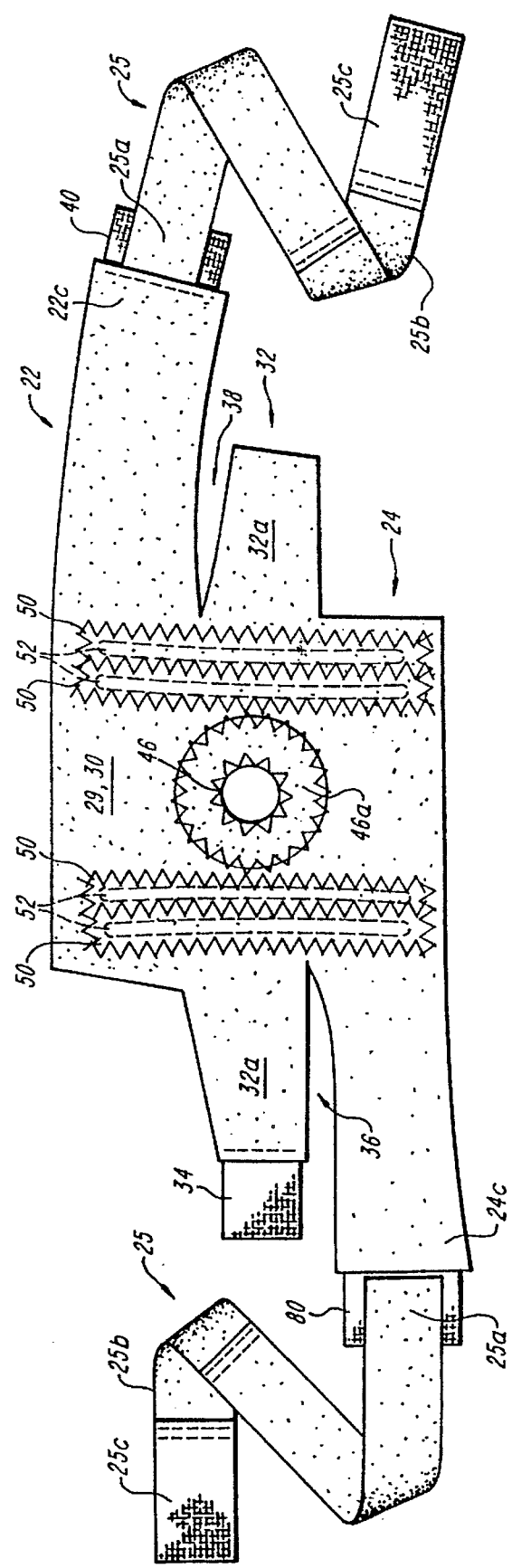
FIG. 4 is a plan view corresponding to FIG. 3 of the inside of the support when laid flat.

The straps extend generally perpendicular to the leg. (As shown in FIGS. 3 and 4, when laid flat they may curve slightly, or have a slightly curved edge, but this curvature is intended to assist the fastener in maintaining the perpendicular orientation despite being wrapped around portions of the leg that normally slope.) A tab 40 of a hook-type material such as the product sold under the trademark Velcro is sewn or otherwise secured to the free ends 22c,24c. An array of minute plastic hooks integral with the tab releasably secure to a layer of minute plastic loops lining one side of a portion 25a (FIG. 4) of a strap extension 25. The portion 25a is formed of a flexible, but relatively inelastic woven material. The section 25b of the strap is formed by a double layer of a resilient stretch elastic material, particularly any of the many standard one-way stretch materials, which is sewn onto one end of the portion 25a. The strap extension terminates in an end tab 25c that carries an array of minute hook-type fasteners, like those used in the tab 40, and oriented to face in the same directions as the hooks of the tab 40 so as to releasably secure to a nylon outer casing 28 that forms an outer layer of a sheet 30 of a flexible elastic material. The sheet is cut as shown in FIGS. 3 and 4 to form the central portion 14, the fasteners 22 and 24 and a central fastener 32 that is aligned with the knee. The components 14, 22, 24 and 34 are preferably formed from a single, integral piece of the sheet material, but it is within the scope of this invention to form each of these components as separate members that are stitched or otherwise secured to one another. The integral one-piece construction has significant advantages in strength, durability and the avoidance of seam bite or rubbing of the skin at the point where components are joined. Also, the strap extensions 25,25 can be formed integrally with these components, up to the resilient portions 25b,25b, but are preferably releasably attached, as described, to allow greater flexibility in positioning the strap extensions.

The sheet material 30 has a central layer 42 of an elastic material that develops a strong spring force when stretched and retains body heat. Neoprene is recommended. The outer casing 28 is adhesively bonded to the neoprene, as is an inner lining 29, also preferably of nylon. The fact that the nylon is woven and therefore has minute openings formed by the constituent threads creates a material to which a hook-type can attach releasably. Used as the outer casing, nylon exhibits good wear, allows clothing to slide freely over the support, and improves the appearance of the support. Used as the inner lining, nylon reduces irritation due to rubbing between the support and the skin of the user, is durable, and absorbs perspiration better than if the neoprene were directly in contact with the skin. Other woven textiles are feasible, but usually they exhibit less wear resistance, less smoothness, or are more costly than nylon. However, cotton terry cloth is another textile which can be used advantageously as the liner where enhanced perspiration absorption and some additional cushioning are desired.

A principal feature of this invention is the central fastener 32. Because it is aligned with the knee, by drawing straps 32a,32a toward one another the central portion 14 and the straps themselves stretch. This stretching exerts a compressive force on the patella directly. This force is adjustable by changing the degree to which the straps 32a,32a are drawn towards one another. When a desired degree of force is reached, the position of the straps is secured by a tab 34 of Velcro hook-type material that is sewn at one of its edges to the free end of one of the straps. It releasably hooks into the openings in the woven textile of the outer casing 28. Because the material of the outer casing itself acts as a loop or "eye" type of fastener material, the tab can be positioned anywhere along the opposite strap 32a, thereby making any adjustment within a wide range possible. This adjustability allows support 10 to fit any of a wide range of sizes of legs while still providing an excellent tailored fit. It also allows the support to be adjusted readily to accommodate variations in the size of the knee or adjoining body portions, as where an injured member is swollen and the degree of swelling changes over time. (Some of the advantages of this invention can be realized by adhering or sewing a tab or strip of conventional loop-type fastener material on the opposite strap 32a, but securing this material in this manner does not allow the strap 32a to stretch freely. This reduces the ability of the support 10 to develop a compressive force. It also reduces its adjustability and tends to develop some twisting of the support about the knee.)

As best seen in FIGS. 2, 3 and 4, generally V-shaped cut-outs 36, 38 in the sides of the support separate and define the central fastener and the upper and lower fasteners. The vertex of each cut-out is at the front or side of the leg, just above or below the knee. The cut-outs widen so that at the back of the leg, behind the knee, there is a gap between each vertically adjacent pair of fasteners. At at the middle of the gap it extends vertically for a maximum distance of about one inch for an adult support. The exact value of this spacing is not critical, but it should be sufficient to avoid buckling or rubbing of the support as the back of the knee as it is flexed through a normal range of motions. The cut-outs also isolate the compressive action of each of the fasteners, so that in combination with their orientation generally perpendicular to the leg, the action of each fastener 22, 24 and 32 is substantially independent of that of the other fasteners. In particular, the protective or therapeutic force on the patella and surrounding tissue is not used to hold the support in place on the leg. The principal securing is performed by the upper and lower fasteners. It is also noteworthy that in contrast to conventional orthopedic appliances and braces, the fasteners 22 and 24 extend vertically along the thigh and calf for a comparatively short distance, about four inches being typical for an adult support. This short height is due to the elasticity and resilience of the material, the one-piece construction of the fasteners, the adjustability of the compressive force, and the ability of each fastener to tailor its contour to that of the user.

The straps 22b, 24b extend from opposite sides of the support to balance the tendency of the straps to twist the support when they are stretched and secured. Tabs 40,40 of a hook-type fastener material are sewn along one edge to the free end of a strap. The tabs releasably and adjustably secure to one of the strap extensions 25,25, or more specifically to a loop or "eye" material arrayed along one surface of the portions 25a,25a. The strap extension is wrapped around the calf or thigh with the portions 25b,25b in a stretched position to develop a compressive force in the associated fastener and in the strap extension itself. The tabs 25c,25c secure directly to the outer casing 28 of the front portions 22a,24a of the fastener. The compressive force is sufficient, combined with the ability of the fastener to conform to the shape of the enclosed portion of the leg and the sliding friction between the leg and the inner lining, to hold the support in a selected location or the leg. In particular, the fasteners 22, 24 stabilize the position of the central portion 14 on the patella despite repeated movement of the leg as in walking, running, climbing, or any other like activity.

In use, particularly of the calf and thigh muscles will repeatedly expand the girth of these members. Also, swelling and continued use will produce a longer term enlargement of the calf and thigh. The resilient suctions 25b,25b accommodated these expansions by stretching in the direction of the strap extension itself. After flexure, the natural resilience of the portions 25b,25b causes them to return to their initial length with no diminution in the original gripping force of the straps. The strap extensions thus avoid slippage of the support along the leg in conjunction with a contraction of the underlying body parts.

In this improved form, the central portion 14 also includes at least one, and preferably a pair of enclosed pockets 50,50 extending generally vertically along the leg for substantially the full height of the support 10 and lying on opposite sides of the patella. Each pocket holds a generally flat, flexible, metallic stay 52 of the type manufactured by Higgins Supply Co. of McGraw, N.Y. The stays 52 themselves flex readily, but when constrained within the pockets they stiffen the support to provide an enhanced degree of mechanical support for an injured knee. The stays 52 thus provide some of the support advantages of a brace, while at the same time providing the flexure, cost and weight advantages of a support. The stays are preferably inserted between a central layer 42 of neoprene and the outer liner 28 with stitching surrounding each stay to secure it in position.

The material 30 is preferably a laminate with a center layer 42 formed of a sheet of neoprene with a uniform thickness in the range of 3/32 to 1/4 inch, and preferably about 1/8 inch. The outer casing 28 is preferably nylon, but can be any woven textile where openings in the weave can act as loops that receive and hold the multitude of plastic hooks extending from the tabs 34 and 40,40. The sheet 30 is cut as shown in FIGS. 3 and 4 in a simple, continuous piece. As noted above, this avoids seam bite and reduces chafing. It also allows the entire support, when secured around a leg, to stretch without constraint in any lateral plane. This arrangement also secures the central portion 14 over the knee while allowing sufficient yielding to accommodate a bending of the knee without thereby applying any significant degree of additional pressure on the knee or having one fastener draw the other toward it.

There has been described an elastic knee support that applies an adjustable direct compressive force on the patella which independently holding the support in a preselected position on the leg with independently adjustable fasteners and despite changes in the size of the leg portions gripped by the fasteners. There has also been described an easy applied fastener which is readily adjusted to any of a wide range of leg sizes and shapes so that it can be made in one size yet fit substantially all persons in a broad category such as adult or child. The knee support described herein has no seam bite, controls chafing and perspiration, and does not buckle at the rear of the knee when it is flexed. It provides these comfort factors while nevertheless offering an enhanced mechanical stability as compared to conventional braces made exclusively of highly flexible materials. It does not interfere with any normal motion of the knee and retains body heat preferentially at the knee. The knee support of this invention is compact. It is also readily manufactured using known materials and fabrication techniques.

While this invention has been described with respect to its preferred embodiments, it will be understood that various modifications and variations will occur to those skilled in the art from the foregoing detailed description and the accompanying drawings. For example, while the central fastener has been described as two straps secured behind the leg, this function could be performed by a single strap. Similarly, the upper and lower fasteners could be two straps that join at their ends. Further, the cut-outs 36,38 can assume a variety of forms, including a mere cut line with substantially no gap. This arrangement will, however, be much more conducive to seam bite and chafing. Further, the upper and lower fasteners can be connected to the central portion by a narrow strip that transmits a vertical stabilizing force, but are otherwise as unobtrusive as possible. The tabs 25c, 34 and 40 can be replaced by metal clips, buckles, pins or a variety of other fasteners, but with some loss of adjustability, increased cost, or risk of damage to the elastic material itself. These and other modifications and variations are intended to fall within the scope of the appended claims.

What is claimed is:

1. An adjustable knee support that is secured to a leg to support the patella and surrounding tissue and which allows a normal range of motion of the knee, comprising a sheet of elastic material having a central support portion that at least surrounds and supports the patella and has upper and lower edges and two side edges adapted to extend along the leg on opposite sides of the patella, an upper fastener extending from said central support portion generally along the upper edge of said central support portion, a lower fastener extending from said central support portion generally along the lower edge of said central support portion, central elastic fastener means secured to the central support portion at at least one of said edges and adapted to be aligned laterally with the patella, said central support portion being stretchable to support the patella directly when said central elastic fastener means is stretched, and means for releasably securing said upper and lower fasteners and said central elastic fastener means when they are stretched in a direction generally perpendicular to the leg to develop a compressive force in said upper and lower fasteners that secures the support on the leg and in said central fastener means to produce said direct support of the patella, said upper and lower fasteners, and said central elastic fastener means being formed with cut-outs to separate and define said central fastener portion from each of said upper and lower fasteners, said cut-outs extending laterally from said two side edges such that said upper and lower fasteners are each spaced vertically from said central fastener means by gaps located generally opposite the patella when said upper and lower fastener are wrapped around the leg and when said releasable securing means are secured.

2. The adjustable knee support of claim 1 wherein said cut-outs have a generally V-shaped configuration.

3. The adjustable knee support of claim 1 wherein said securing means includes a tab of material carrying an array of hook fasteners on at least one surface thereof and a second piece material that has a plurality of mating loop fasteners that when pressed together replaceably secure said upper and lower fasteners around the leg and replaceably secure the central support portion over the knee, all with an adjustable degree of compression depending on the relatively lateral location of said tab on second piece of material and therefore the degree to which said upper and lower fasteners and said central elastic fastener means are stretched.

4. The adjustable knee support of claim 1, wherein said upper and lower fasteners are each adapted to extend laterally for a sufficient distance to wrap around the leg.

5. The adjustable knee support of claim 1 wherein said sheet of elastic material comprises a laminate of central layer of an elastic material, an outer casing of a woven textile material that mates with a hook fastener material, and an inner lining formed of a textile material.

6. The adjustable knee support of claim 5 wherein said central layer of sheet material is neoprene and said outer casing and said inner lining are formed of nylon.

7. The adjustable knee support of claim 5 wherein said upper and lower fasteners are each adapted to extend vertically on the leg about 4 inches.

8. The adjustable knee support of claim 7 wherein said central fastener means has a vertical height of about 2 inches and said gaps above and below said central fastener means each extending vertically about 1 inch.

9. The adjustable knee support of claim 1 wherein said central portion contains an internal opening adapted to generally circle the patella.

10. The adjustable knee support of claim 1 wherein said upper and lower fasteners extend from said central support portion in opposite directions.

11. The adjustable knee support of claim 1 wherein said upper and lower fasteners each comprise strap portion that extend from opposite sides of said central support portion.

* * * * *